United States Patent [19]

Sundermann

[11] 4,060,541

[45] Nov. 29, 1977

[54] AROMATIC CYANIC ACID ESTERS

[75] Inventor: Rudolf Sundermann, Leverkusen, Germany

[73] Assignee: Bayer Aktiengesellschaft, Leverkusen, Germany

[21] Appl. No.: 655,362

[22] Filed: Feb. 5, 1976

[30] Foreign Application Priority Data

Feb. 22, 1975 Germany .............................. 2507746

[51] Int. Cl.² .......................................... C07C 122/00
[52] U.S. Cl. ...................... 260/453 AR; 260/453 AM; 260/453 P; 260/463; 260/939
[58] Field of Search .................. 260/453 AR, 453 AM

[56] References Cited

U.S. PATENT DOCUMENTS

| 3,553,244 | 1/1971 | Grigat et al. | 260/453 AR |
| 3,595,900 | 7/1971 | Loudas et al. | 260/453 AR |
| 3,763,206 | 10/1973 | Brunetti | 260/453 AR |

Primary Examiner—Dolph H. Torrence
Attorney, Agent, or Firm—Burgess, Dinklage & Sprung

[57] ABSTRACT

Aromatic cyanic acid esters having a free hydroxyl group which is not sterically hindered are prepared by reacting aromatic dihydroxy and polyhydroxy compounds with cyanogen halide in aqueous solution in the presence of a water-immiscible organic solvent and an inorganic base. Aromatic cyanic acid esters prepared by the process have the formula $$(HO)_{\overline{m}}-AR-(OCN)_n \qquad (V)$$

wherein
Ar is optionally substituted aromatic and $n$ and $m$ are the same or different and are one of the numbers from 1 to 5, with the sum $m$ and $n$ being not greater than the number of replaceable hydrogen atoms in the radical Ar.

3 Claims, No Drawings

AROMATIC CYANIC ACID ESTERS

BACKGROUND

This invention relates to a process for the preparation of aromatic cyanic acid esters having a free hydroxyl group, and to new aromatic cyanic acid esters.

It is known to react monophenols and polyphenols with cyanogen halides to give aromatic cyanic acid esters (German Published Specification No. 1,195,764) in which reaction all phenolic hydroxyl groups are esterified. Furthermore, it has been disclosed that this method however gives, starting from 2,6-di-tert.-butyl-hydroquinone or di-tert.-amylhydroquinone, the corresponding 1-hydroxy-2,6-di-tert.-butyl- or di-tert.amyl-phenyl (4)-cyanic acid ester, respectively, which is ascribed to the strong steric screening of the 1-hydroxyl group German Published Specification No. 2,155,413; C.R. Acad. Sc. Paris, 260 3,985 to 3,988), though aromatic cyanic acid esters were originally obtained from sterically hindered phenols (German Pat. No. 1,079,650).

SUMMARY

It has now been found, surprisingly, that aromatic cyanic acid esters with a free hydroxyl group, which is not sterically hindered, are obtained when aromatic dihydroxy compounds and polyhydroxy compounds are reacted with cyanogen halide in aqueous solution in the presence of a water-immiscible organic solvent and of an inorganic base.

DESCRIPTION

Aromatic dihydroxy compounds and polyhydroxy compounds which can be used are all aromatic, including aromatic-heterocyclic, compounds with at least two phenolic hydroxyl groups, of which a large number is known.

In particular, they correspond to the general formula

$$(HO)_m-Ar-(OH)_n \quad (I)$$

in which
Ar denotes an optionally substituted aromatic radical and
n and m are identical or different and represent one of the numbers from 1 to 5, with the sum $m + n$ being not greater than the number of hydrogen atoms, capable of replacement, of the radical Ar.

Possible radicals Ar are mononuclear and polynuclear aromatic and heteroaromatic radicals, and two or more of these radicals can also be linked by bridge members.

Alkyl and halogen should be mentioned preferentially as substituents of the optionally substituted radicals Ar.

Alkyl radicals which should be mentioned are straight-chain and branched, especially lower, alkyl radicals with up to 9, preferably with up to 6, C atoms, such as methyl, ethyl, propyl, isopropyl, butyl, isobutyl, ter.-butyl, amyl, isoamyl and the other isomeric pentyl radicals and the isomeric hexyl radicals. Methyl, ethyl, propyl and isopropyl should be mentioned in particular.

Halogens which should be mentioned are fluorine, chlorine, bromine and iodine, preferably chlorine and bromine.

A preferred group of the compounds of the formula I are diphenols and polyphenols of the formula

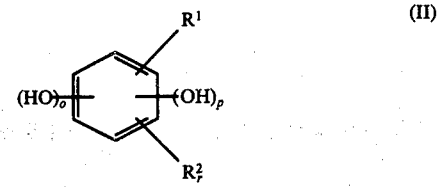

in which
$R^1$ and $R^2$ are identical or different and represent alkyl or halogen and
o and p are identical or different and represent one of the numbers from 1 to 5 and
q and r are identical or different and represent one of the numbers 0, 1 or 2,
with the sum of the numbers o, p, q and r being at most 6.

Preferably, o and p represent 2, and especially 1.

The following may be mentioned as examples of such diphenols and polyphenols: hydroquinone, resorcinol, 2,4-dimethylresorcinol, 4-chlororesorcinol and tetramethylhydroquinone.

A further group of the compounds of the formula I correspond to the general formula

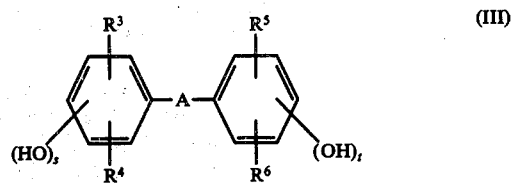

in which
$R^3$, $R^4$, $R^5$ and $R^6$ are identical or different and represent hydrogen, halogen or alkyl,
A represents a simple bond, a divalent alkyl radical, optionally substituted by lower alkyl, with up to 6, preferably with up to 4, C atoms, an optionally substituted 5-membered or 6-membered cycloaliphatic radical or a hetero-atom, such as oxygen or sulphur, or denotes a sulphonyl (—SO$_2$—) or carbonyl (—CO—) group or a carbonate (—O(-CO)O—) radical or the radical

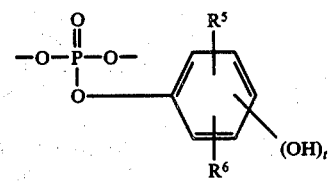

in which
$R^5$ and $R^6$ have the abovementioned meaning and
t has the meaning mentioned below, and
s and t are identical or different and represent one of the numbers from 1 to 5, preferably 1 and 2, and especially 1.

Substituents of the divalent alkyl radical (A) which should be mentioned in particular are lower alkyl radicals, preferably methyl, and phenyl.

Possible examples of compounds of the formula III are 4,4'-dihydroxydiphenyl, 4,4'-dihydroxydiphenylsulphone, 4,4'-dihydroxydiphenyl ether, 1,1-bis-(4-hydroxyphenyl)-ethane, 2,2-bis-(4-hydroxyphenyl)-propane, 2,2-bis-(3,5-dimethyl-4-hydroxyphenyl)-propane, 2,2-bis-(3,5-dichloro 4-hydroxyphenyl)-propane, 1,1-bis-(4-hydroxyphenyl)-cyclohexane, 4,4'-dihydroxybenzophenone, 4,4'-bis-(4-hydroxyphenyl-isopropyl)-diphenyl carbonate and 4,4',4''-tris-(p-hydroxyphenylisopropyl)-phenyl phosphate.

Furthermore, the following may be mentioned as examples of compounds of the formula I: dihydroxynaphthalenes, such as 1,4-, 1,5-, 1,6-, 1,7-, 2,6- and 2,7-dihydroxynaphthalene.

Possible cyanogen halides are above all cyanogen chloride and cyanogen bromide, which are technically easily accessible, in particular cyanogen chloride.

Examples of possible water-immiscible solvents are: aromatic hydrocarbons, such as benzene, toluene and xylenes; aliphatic and aromatic chlorohydrocarbons, such as dichloromethane, dichloroethane, chlorobenzene and dichlorobenzene; aliphatic and aromatic nitrohydrocarbons, such as nitromethane and nitrobenzene; aliphatic ethers, such as diethyl ether, diisopropyl ether and diisobutyl ether.

The following may be mentioned as examples of inorganic bases: the oxides, hydroxides, carbonates and bicarbonates of the alkali metals (lithium, sodium, potassium, rubidium and caesium), preferably of sodium and potassium; sodium hydroxide and potassium hydroxide, sodium bicarbonate and potassium bicarbonate, and sodium carbonate and potassium bicarbonate may be mentioned in particular.

The process according to the invention is in general carried out in the temperature range of between −40° C and +65° C, preferably between 0° and 30° C. If cyanogen chloride is used, the reaction is preferably carried out at a temperature below its boiling point (13° C); if cyanogen bromide is used, higher temperatures, for example above 50° C, can also be of advantage.

In general, the process according to the invention is carried out by suspending and/or dissolving the aromatic dihydroxy compound or polyhydroxy compound and cyanogen halide in the mixture of water and water-immiscible solvent and then adding the inorganic base, if appropriate dissolved in water. However, it is also possible first to take the aromatic dihydroxy or polyhydroxy compound in the mixture of water and solvent and add the cyanogen halide and the inorganic base, both in solution if appropriate; equally, it is also possible first to take the cyanogen halide, if appropriate dissolved in water and/or organic solvent, and to add the aromatic dihydroxy or polyhydroxy compound and the inorganic base, both also dissolved, if appropriate, in water and/or organic solvents.

The cyanogen halide can be employed as a solid, liquid or gas.

In the process according to the invention, the aromatic dihydroxy or polyhydroxy compound, cyanogen halide and inorganic base can be employed in stoichiometric amounts, relative to the number of hydroxyl groups to be reacted; in general, however, it can be advantageous to use an excess of cyanogen halide of up to 100 mol%, preferably of up to 50 mol% and especially of up to 30 mol%.

An excess of inorganic base does not have to be avoided and is generally not detrimental.

Suitably, the process according to the invention is carried out in the pH range of 3.5 – 9.5, especially between 6.5 and 9.0.

The process according to the invention can be explained, by way of example, by the following equation for the example of 2,2-bis-(4-hydroxyphenyl)-propane

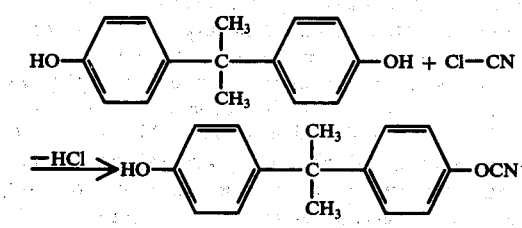

The new aromatic cyanic acid esters having a free hydroxyl group in general correspond to the formula $$(HO)_{\overline{m}}\text{—}AR\text{——}(OCN)_n \qquad (V)$$

in which

Ar, $n$ and $m$ have the abovementioned meaning.

A group of compounds which can be obtained in accordance with the process of the invention comprises hydroxyphenyl cyanic acid esters of the formula

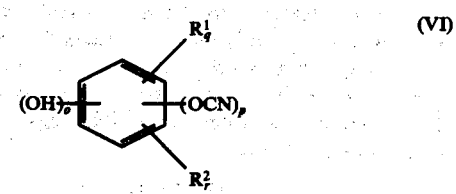

in which $R^1$, $R^2$, $o$, $p$, $q$ and $r$ have the abovementioned meaning.

The following may be mentioned as examples of such esters: m-hydroxyphenyl cyanate, p-hydroxyphenyl cyanate, 4,6-dimethyl-3-hydroxyphenyl cyanate, 2,5-di-tert.-butyl-4-hydroxyphenyl cyanate, 2,3,5,6-tetramethyl-4-hydroxyphenyl cyanate and 5-methyl-3-hydroxyphenyl cyanate.

A further preferred group of compounds which can be obtained in accordance with the process of the invention corresponds to the general formula

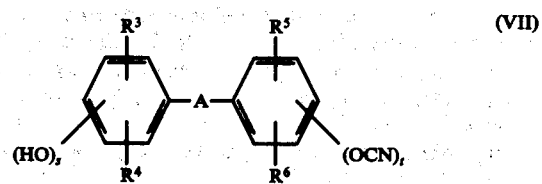

in which $R^3$, $R^4$, $R^5$, $R^6$, A, $s$ and $t$ have the abovementioned meaning.

The following may be mentioned as examples of such compounds: 4-hydroxy-4'-cyanato-diphenyl, 4-hydroxy-4'-cyanato-diphenyl-sulphone, 4-hydroxy-4'-cyanato-diphenyl ether, 4-hydroxy-4'-cyanato-benzophenone, 1-(4-hydroxyphenyl)-1-(4-cyanatophenyl)-ethane, 2-(4-hydroxyphenyl)-2-(4-cyanatophenyl)-propane, 2-(3,5-dimethyl-4-hydroxyphenyl)-2-(3,5-dimethyl-4-cyanatophenyl)-propane, 2-(3,5-dichloro-4-hydroxyphenyl)-2-(3,5-dichloro-4-cyanato-phenyl)-propane, 1-(4-hydroxyphenyl)-1-(4-cyanatophenyl)- cyclohexane and 4-(4-hydroxyphenyl-isopropyl)-4'-(4-cyanatophenyl-isopropyl)-diphenyl carbonate.

Where compounds of the formula III are used as starting compounds, it is also possible to obtain, in accordance with the process of the invention, compounds of the formula

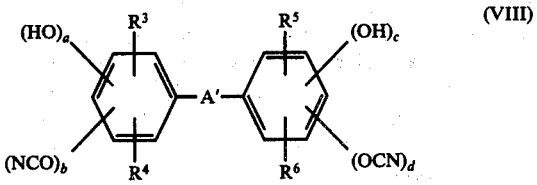

and of the formula

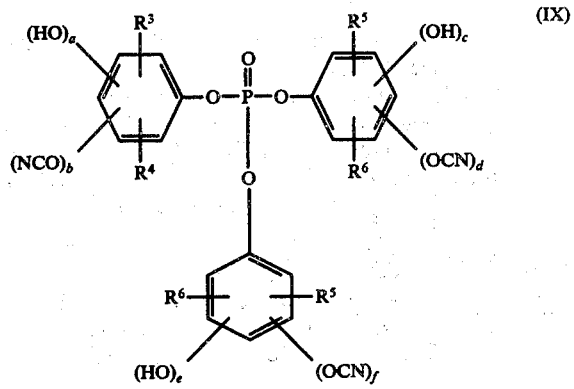

in which
$R^3$, $R^4$, $R^5$ and $R^6$ have the abovementioned meaning.
$A'$ represents a simple bond, a divalent alkyl radical, optionally substituted by lower alkyl, with up to 6, preferably with up to 4, C atoms, a divalent alkyl radical, optionally substituted by lower alkyl, with up to 6, preferably with up to 4, C atoms, an optionally substituted 5-membered or 6-membered cycloaliphatic radical or a hetero-atom such as oxygen or sulphur, or denotes a sulphonyl or carbonyl group or a carbonate radical and $a$, $b$, $c$, $d$, $e$ and $f$ are identical or different and denote one of the numbers 0, 1 or 2, but the sums $a + b$, $c + d$ and $e + f$ cannot be greater than 3.

Preferably, of the pairs of numbers $a$ and $b$, $c$ and $d$, and $e$ and $f$, independently of one another, one number in each case represents 0 and the other represents 1.

Further, compounds which can be obtained according to the process of the invention, are naphthalene derivatives of the formulae

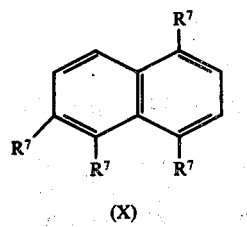 and 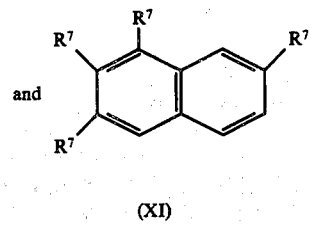

(X)                    (XI)

in which
$R^7$ denotes hydrogen, the hydroxyl group or the cyanato group and in each case at least one radical $R^7$ represents the hydroxyl group and at least one radical $R^7$ represents the cyanato group, whilst the two other radicals $R^7$ can have a different meaning.

As examples of such compounds there may be mentioned: 4-hydroxy-α-naphthyl cyanate, 5-hydroxy-α-naphthyl cyanate, 6-hydroxy-β-naphthyl cyanate, 7-hydroxy-β-naphthyl cyanate, 6-hydroxy-α-naphthyl cyanate and 5-hydroxy-β-naphthyl cyanate.

The aromatic cyanic acid esters, containing hydroxyl groups, which are obtainable in accordance with the process of the invention, are valuable intermediate products. They can easily be polymerised to give polyiminocarbonic acid phenyl esters or be trimerised by acid or basic catalysis to give s-triazines, which are used as heat-stabilisers and cross-linking agents for polycondensations. Furthermore, the new compounds are good catalysts for the polytrimerisation of polyfunctional cyanic acid esters to give valuable high-molecular s-triazines.

According to the process of German Published Specification No. 1,720,740, mouldings based on polyfunctional aromatic cyanic acid esters are prepared by combining the polyfunctional aromatic cyanic acid esters with pulverulent and/or fibrous fillers or reinforcing agents, a thermal pretreatment being carried out before or after the combination. According to the examples, a time of 48 hours is required for this pretreatment at 120° C. For completely pure 2,2-bis-(4-cyanatophenyl)-propane, our own experience has shown that a time far in excess of 50 hours is required even at 200° C. If, on the other hand, 4-(4-hydroxyphenylisopropyl)-phenyl cyanate is added to the same material before the thermal treatment, the thermal pretreatment can be carried out at 150° C in a substantially shorter time.

EXAMPLE 1

23 g (0.1 mol) of 2,2-bis-(4-hydroxyphenyl)-propane are suspended in 500 ml of water and 200 ml of methylene chloride. After cooling to 0° C, 15 ml (0.3 mol) of cyanogen chloride are added and 10.6 g (0.1 mol) of $Na_2CO_3$, dissolved in 50 ml of water, are then added over the course of about 90 minutes, with vigorous stirring, in such a way that a pH value of 7.5 to 8.5 is maintained in the reaction mixture. In the course thereof, the 2,2-bis-(4-hydroxyphenyl)-propane dissolves completely. During the reaction, the temperature is kept at about 0° C by cooling, and thereafter the reaction is terminated, at this temperature, by dropwise addition of 1 N NaOH, this dropwise addition being carried out in such a way that a pH value of about 8.5 is maintained constantly and about 150 ml of N NaOH are consumed.

After completion of the reaction, the organic phase is separated off and the solvent is distilled off. Extractive boiling of the residue which remains, with ligroin (boiling range 90° – 110° C), gives 25 g (99% of theory) of 4-(4-hydroxyphenylisopropyl)-phenyl cyanate in the form of colourless needles of melting point 75° C.

EXAMPLE 2

22.0 g (0.2 mol) of resorcinol were suspended in 500 ml of water and 300 ml of methylene chloride. After cooling to 0° – 3° C, 30 ml (0.6 mol) of cyanogen chloride were added and 21.2 g (0.2 mol) of $Na_2CO_3$, dissolved in 100 ml of water, were then added dropwise over the course of 2 hours, with vigorous stirring, in such a way that a pH value of 7.5 to 8.0 was maintained constantly. The reaction temperature was kept at 0° to 3° C by cooling. The reaction was then terminated by addition of 1 N NaOH, the amount of 1 N NaOH added being such that a pH value of 8.0 is not excceded and ultimately persists as the final value.

After the end of the reaction, the organic phase is separated off and washed with 50 ml of water, and the solvent is stripped off at room temperature. 26.0 g (96% of theory) of 3-hydroxy-phenyl cyanate are obtained.

IR spectrum: strong OH band at 2.9 μ, OCN band at 4.5 μ.

EXAMPLE 3

28.4 g (0.1 mol) of 2,2-bis-(3,5-dimethyl-4-hydroxyphenyl)-propane are suspended in 500 ml of water and 300 ml of dichloromethine. After cooling to 0° C, 15 ml (0.3 mol) of cyanogen chloride are added. 10.6 g (0.1 mol) of Na$_2$CO$_3$, dissolved in 50 ml of water, are then added dropwise over the course of 2 hours, with vigorous stirring, in such a way that a pH value of between 7.5 and 8.5 is maintained constantly in the reaction mixture. At the same time, the reaction temperature is kept at about 0° C by cooling. Thereafter, the reaction is terminated by slow addition of 1 N NaOH, the 1 N NaOH being added in such a way that a pH value of 7.5 to 8.0 is constantly maintained in the reaction mixture and persists as the final value. After the end of the reaction, the organic phase is separated off, washed with 50 ml of water and concentrated at room temperature. 30.8 g (99% of theory) of 2-(3,5-dimethyl-4-hydroxyphenyl)-2-(3,5-dimethyl-4-cyanatophenyl)-propane are obtained as the residue.

IR spectrum: strong OH band at 2.9 μ, OCN band at 4.5 μ.

EXAMPLE 4

36.6 g (0.1 mol) of 2,2-bis-(3,5-dichloro-4-hydroxyphenyl)-propane are suspended in 500 ml of water and 400 ml of methylene chloride. After cooling to about 0° to 3° C, 20 ml (0.4 mol) of cyanogen chloride are added. A solution of 10.6 g of Na$_2$CO$_3$ in 50 ml of water is added dropwise over the course of 90 minutes, with vigorous stirring, in such a way that the pH value of the reaction mixture is constantly kept in the range between 7.5 and 8.5. Thereafter, 1 N NaOH is added in such a way that a pH value of the reaction mixture of about 8.0 is maintained, and persists as the final value. Thereafter, the organic phase is separated off, washed with 100 ml of water and concentrated at room temperature. 39 g (99% of theory) of 2-(3,5-dichloro-4-hydroxyphenyl)-2-(3,5-dichloro-4-cyanatophenyl)-propane are obtained as the residue.

IR spectrum: strong OH band at 2.9 μ, OCN band at 4.5 μ.

EXAMPLE 5

86.8 g (0.1 mol) of 1,1-bis-(4-hydroxyphenyl)-cyclohexane are suspended in 500 ml of water and 300 ml of methylene chloride at about 0° to 3° C. 20 ml (0.4 mol) of cyanogen chloride are added to this suspension and a solution of 10.6 g (0.1 mol) of Na$_2$CO$_3$ in 50 ml of water is added dropwise over the course of 90 minutes at the same temperature, with vigorous stirring, in such a way that a pH value between 7.5 and 8.5 is maintained in the reaction mixture. Thereafter, 1 N NaOH is added at 0° C in such a way that the abovementioned pH value is maintained, and persists as the final value. Thereafter, the organic phase is separated off and washed with 50 ml of water and the solvent is stripped off at room temperature. 29 g (99% of theory) of 1-(4-hydroxyphenyl)-1-(4-cyanatophenyl)-cyclohexane are thus obtained.

IR spectrum: strong OH band at 2.9 μ, OCN band at 4.5 μ.

EXAMPLE 6 a. One part by weight of triethylamine is added to 100 parts by weight of 4-(4-hydroxyphenylisopropyl)-phenyl cyanate and the mixture is warmed to 200° C for 5 hours. A hard clear polymer of pale yellow colour is obtained.

b. One drop of triethylamine is added to 29 g of the 1-(4-hydroxyphenyl)-1-(4-cyanatophenyl)-cyclohexane obtained according to Example 5 and the mixture is then heated to 170° C for 5 hours. A hard, pale yellow polymer is thus obtained.

EXAMPLE 7

To reach the so-called B-stage according to the process of German Published Specification No. 1,720,740, more than 50 hours are required at 200° C if pure 2,2-bis-(4-cyanatophenyl)-propane is used. On adding the amount of 4-(4-hydroxyphenylisopropyl)-phenyl cyanate indicated in Table I below (percent by weight), relative to 2,2-bis-(4-cyanatophenyl)-propane, merely the time indicated in Table I below is required at a temperature of 150° C.

Table I

| Per cent by weight | Time (hours) |
| --- | --- |
| 0.5 | 16 to 20 |
| 1.0 | 12 to 14 |
| 2.0 | 8 to 10 |

EXAMPLE 8

In the manufacture of mouldings using resorcinol dicyanate in accordance with the process of German Published Specification No. 1,720,740, pure resorcinol dicyanate must be heated to 150° C for more than 20 hours in order to achieve the so-called B-state and obtain an easily processable prepolymer.

On adding 1.0 percent by weight of 3-hydroxyphenyl cyanate to the pure resorcinol dicyanate, the corresponding prepolymer is obtained in 3 to 5 hours at 150° C.

What is claimed is:
1. Aromatic cyanic acid esters of the formula

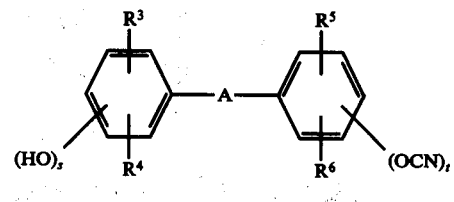

wherein
R$^3$, R$^4$, R$^5$ and R$^6$ are the same or different and are hydrogen, halogen or alkyl,
A is a bond between the aromatic rings or divalent alkyl with up to 6 carbon atoms, optionally substituted by lower alkyl, optionally substituted 5-membered or 6-membered cycloaliphatic, sulphonyl (—SO$_2$—) or carbonyl (—CO—),
wherein
s and t are the same or different and are one of the numbers from 1 to 5.

2. Cyanic acid esters of the formula

(HO)$_m$—AR—(OCN)$_n$  (V)

wherein
Ar is optionally substituted aromatic and $n$ and $m$ are the same or different and are one of the numbers from 1 to 5, with the sum $m$ and $n$ being not greater than the number of replaceable hydrogen atoms in the radical Ar, said ester being from the group of
4-(4-Hydroxyphenylisopropyl)-phenyl cyanate,
2-(3,5-Dimethyl-4-hydroxyphenyl)-2-(3,5-dimethyl-4-cyanatophenyl)-propane,
2-(3,5-Dichloro-4-hydroxyphenyl)-2-(3,5-dichloro-4-cyanatophenyl)-propane, and
1-(4-Hydroxyphenyl)-1-(4-cyanatophenyl)-cyclohexane.

3. Aromatic cyanic acid esters of the formula

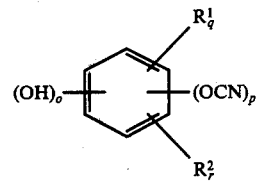

wherein
$R^1$ and $R^2$ are the same or different and are alkyl or halogen and
$o$ and $p$ are identical or different and represent one of the numbers from 1 to 5 and
$q$ and $r$ are identical or different and represent one of the numbers 0, 1 or 2
with the sum of the numbers $o$, $p$, $q$ and $r$ being a maximum of 6 selected from the group consisting of m-hydroxyphenyl cyanate, p-hydroxyphenyl cyanate, 4,6-dimethyl-3-hydroxyphenyl cyanate, 2,3,5,6-tetramethyl-4-hydroxyphenyl cyanate and 5-methyl-3-hydroxyphenyl cyanate.

* * * * *

UNITED STATES PATENT AND TRADEMARK OFFICE
CERTIFICATE OF CORRECTION

PATENT NO. : 4,060,541
DATED : November 29, 1977
INVENTOR(S) : Rudolf Sundermann It is certified that error appears in the above–identified patent and that said Letters Patent are hereby corrected as shown below:

Column 2, line 5, "$R^1$" should read -- $R^1_q$ --.

Signed and Sealed this

Second Day of May 1978

[SEAL]

Attest:

RUTH C. MASON
Attesting Officer

LUTRELLE F. PARKER
Acting Commissioner of Patents and Trademarks